United States Patent [19]

Atwal

[11] Patent Number: 5,164,509
[45] Date of Patent: Nov. 17, 1992

[54] BENZODIAZOLO ANALOGS

[75] Inventor: Karnail Atwal, Newtown, Pa.

[73] Assignee: E. R. Squibb & Sons, Inc., Princeton, N.J.

[21] Appl. No.: 618,277

[22] Filed: Nov. 26, 1990

[51] Int. Cl.$^5$ .......................................... C07D 498/04
[52] U.S. Cl. ...................................... 548/126; 548/256
[58] Field of Search ................................ 548/126, 256

[56]         References Cited
          U.S. PATENT DOCUMENTS

| 4,575,511 | 3/1986 | Evans et al. | 514/456 |
| 4,900,752 | 2/1990 | Seto | 514/364 |

FOREIGN PATENT DOCUMENTS

| 0327127 | 8/1989 | European Pat. Off. . |
| 0344747 | 12/1989 | European Pat. Off. . |
| 02-004791 | 1/1990 | Japan . |
| WO91/14690 | 10/1991 | PCT Int'l Appl. . |

OTHER PUBLICATIONS

Mozolis et al., *Russian Chemical Reviews*, 42 (7), 1973, pp. 587–595.
Rasmussen et al., *Synthesis*, (1988), pp. 456–459.
J. M. Evans et al., *J. Med. Chem.*, 1983, 26, 1582–1589.
V. A. Ashwood et al., *J. Med. Chem.*, 1986, 29, 2194–2201.

*Primary Examiner*—Robert Gerstl
*Attorney, Agent, or Firm*—Theodore R. Furman, Jr.

[57]              ABSTRACT

Novel potassium channel activators of the formula

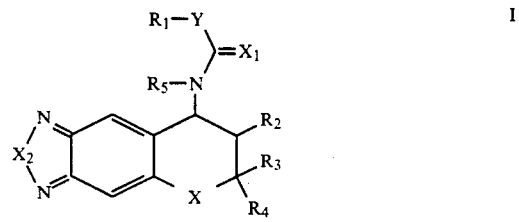

where Y, X, $X_1$, $X_2$(N or O), and $R_1$–$R_4$ are as defined herein, are disclosed.

5 Claims, No Drawings

BENZODIAZOLO ANALOGS

FIELD OF THE INVENTION

The present invention relates to benzodiazolo analogs having potassium channel activating activity, and more particularly concerns such compounds which are useful for cardiovascular disorders.

SUMMARY OF THE INVENTION

In accordance with the present invention novel compounds useful, for example, as antiischemic agents, are disclosed. These compounds have the general formula

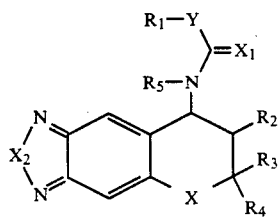

I and pharmaceutically acceptable salts thereof, wherein X is —O—,

or a single bond;
$X_1$ is —O—, —S— or N—C≡N;
$X_2$ is —O—or —NH—;
Y is —NR$_6$, —O—, —S— or

$R_1$ is aryl, arylalkyl, heterocyclo or (heterocyclo)alkyl;
$R_2$ is hydrogen, hydroxy,

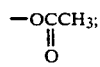

$R_3$, $R_3'$, $R_4$ and $R_4'$ are independently selected from hydrogen, alkyl or arylalkyl, or, $R_3$ and $R_4$ (or $R_3'$ and $R_4'$) taken together with the carbon atom to which they are attached form a 5- to 7-membered ring; with the proviso that if $R_3$ and/or $R_4$ are other than hydrogen, then $R_3'$ and $R_4'$ are each hydrogen;

$R_5$ and $R_6$ are each independently hydrogen, alkyl or arylalkyl; or $R_1$ and $R_5$, or, $R_5$ and $R_6$ or $R_1$ and $R_6$ taken together can form a 5- to 7-membered ring, which may further include an aryl group fused to 2 carbon atoms of such 5- to 7-membered ring; and, $R_7$ is hydrogen, hydroxy, alkyl or O-alkyl.

DETAILED DESCRIPTION OF THE PRESENT INVENTION

This invention in its broadest aspects relates to the benzodiazolo analogs of formula I above, to compositions and the methods of using such compounds. The compounds of formula I are useful, for example, as cardiovascular agents.

The term "alkyl" used in defining various symbols refers to straight or branched chain saturated hydrocarbon radicals having up to eight carbons, preferably from one to five carbons. Similarly, the terms "alkoxy" and "alkylthio" refer to such alkyl groups attached to an oxygen or sulfur.

The term "alkenyl" refers to straight or branched chain hydrocarbon radicals having from two to eight carbons and one double bond, preferably three to five carbons. The term "alkynyl" refers to straight or branched chain hydrocarbon radicals having from two to eight carbons and one triple bond, preferably three to five carbons.

The term "cycloalkyl" refers to saturated carbocyclic rings of 3 to 7 carbon atoms with cyclopropyl, cyclopentyl and cyclohexyl being most preferred.

The term "halo" or "halogen" refers to chloro, bromo, iodo and fluoro.

The term "halo substituted alkyl" refers to such alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term "aryl" refers to phenyl, 1-naphthyl, 2-naphthyl or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, N($R_3$)CO-$R_3$, N($R_9$)COCF$_3$, N($R_9$)CO-amino, N($R_9$)CO-substituted amino, COR$_9$, COOR$_9$ (wherein R$_9$ is R$_5$, aryl and haloalkyl),

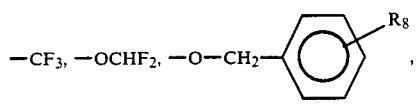

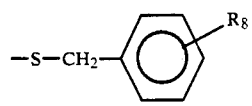

(wherein R$_8$ is hydrogen, alkyl of 1 to 4 carbons, alkoxy of 1 to 4 carbons, alkylthio of 1 to 4 carbons, halo, hydroxy or CF$_3$), —O—CH$_2$-cycloalkyl, or —S—CH$_2$—cycloalkyl, and di-substituted phenyl, 1-naphthyl, 2-naphthyl wherein said substituents are selected from methyl, methoxy, methylthio, halo, CF$_3$, nitro, amino, and OCHF$_2$.

Preferred aryl groups include unsubstituted phenyl and monosubstituted phenyl wherein the substituents are nitro, halo, —CF$_3$, alkyl, cyano or methoxy.

The term "heterocyclo" refers to fully saturated or unsaturated rings of 5 or 6 atoms containing one or two O and S atoms and/or one to four N atoms provided that the total number of hetero atoms in the ring is 4 or less. The hetero ring is attached by way of an available atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH-alkyl wherein alkyl is of 1 to 4 carbons, —N(alkyl)$_2$ wherein alkyl is of 1 to 4 carbons, CF$_2$, or OCHF$_2$ or such monocyclic and bicyclic rings wherein two or three available carbons have substituents selected from methyl, methoxy, methylthio, halo, CF$_3$, nitro, hydroxy, amino and OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

The compounds of formula I wherein Y is —NR$_3$, X$_1$ is —NCN can be prepared by treatment of a thiourea of the formula

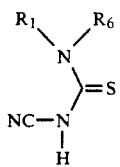       II with an amine of the formula

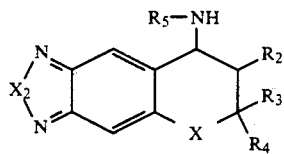       III in the presence of a coupling agent, e.g., a carbodiimide, in an organic solvent, such as dimethylformamide, tetrahydrofuran, acetonitrile or dichloromethane. If dicyclohexylcarbodiimide is used, it should be employed with an acid source. Preferably, the carbodiimide is of the formula

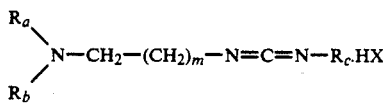       A wherein X is halogen, R$_a$, R$_b$ and R$_c$ are independently alkyl, cycloalkyl, phenyl, phenylalkyl, cycloalkylalkyl or R$_a$ and R$_b$ taken together with the nitrogen atom to which they are attached form 1-pyrrolidinyl, 1-piperidinyl, 4-morpholinyl, 4-thiomorpholinyl, 4-alkyl-1-piperazinyl or 4-phenylalkyl-1-piperazinyl. Most preferably the carbodiimide is 1-(3-dimethylaminopropyl)-3-ethylcarbodiimide hydrochloride.

The thiourea of formula II, wherein R$_6$ is hydrogen can be prepared by heating an isothiocyanate of the formula $$R_1N=C=S \qquad \text{IV}$$

with either monosodium cyanamide or with cyanamide in the presence of an organic base, such as triethyl amine.

The other thioureas of formula II, i.e. where R$_6$ is other than hydrogen, can be prepared by standard methods described in the literature, such as by C. R. Rasmussen, F. J. Villani, Jr., L. E. Weaner, B. E. Reynolds, A. R. Hood, L. R. Hecker, S. O. Nortey, A. Hanslin, M. J. Costanzo, E. T. Powell, A. J. Molinari, *Synthesis*, 1988, p. 456, and V. V. Mozolis and S. P. Locubaitite, *Russian Chemical Reviews*, 1973, 42, 587.

The aminoalcohol of formula III wherein R$_2$ is hydroxy, X and X$_2$ are each —O— can be prepared according to EP 327-127-A by first treating a compound of the formula

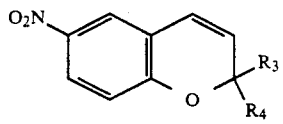       V with a reducing agent, e.g., SnCl$_2$. 2H$_2$O in a solvent such as ethanol to provide an intermediate of the formula

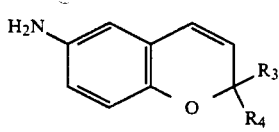       VI which can thereafter be treated in a solvent, e.g., dichloromethane with a base, e.g., triethylamine and thereafter with an acylating agent, e.g., acetyl chloride to provide a compound of the formula

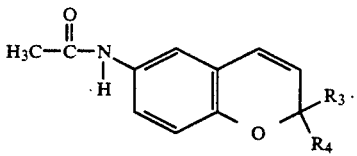       VII

Compound VII is nitrated with nitric acid in acetic acid to provide an intermediate of the formula

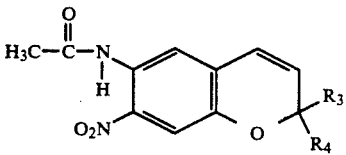       VIII which can be treated with N-bromosuccinide, in a solvent, e.g., dimethylsulfoxide to provide a bromohydrin of formula

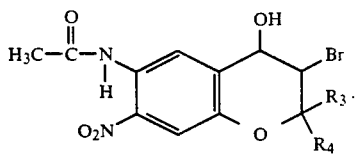
IX

Compound IX is thereafter treated with an acid, e.g., hydrochloric acid in a solvent, e.g., ethanol, to provide compounds of the formula

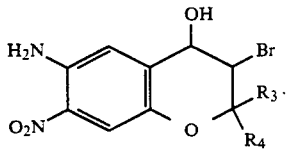
X

In turn, compound X can be treated with a base, e.g., potassium hydroxide in a solvent, such as ethyl ether, to provide intermediates of the formula

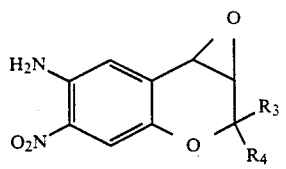
XI which can be treated with a base such as sodium hydroxide in a solvent, e.g., ethanol, followed by treatment with sodium oxychloride to provide

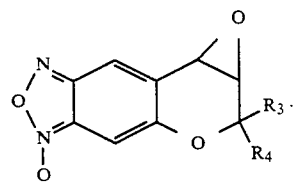
XII

Treatment of intermediate XII with a reducing agent, e.g., triethyl phosphite, in a solvent, such as benzene, provides the intermediates of the formula

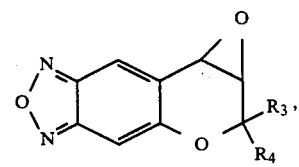
XIII which can be treated with ammonium hydroxide, in solvents, such as ethanol and tetrahydrofuran, to provide aminoalcohols of formula III where $R_1$ is hydrogen, $R_2$ is trans-hydroxy and X and $X_2$ are each —O—.

Compounds of formula V can be prepared by methods described in the literature, such as by J. M. Evans, C. S. Fake, T. C. Hamilton, R. H. Poyser, E. A. Watts, *J. Med. Chem.* 1983, 26, 1582 and *J. Med. Chem.* 1986, 29, 2194.

Amines of formula III wherein X is —O— and $X_2$ is NH, $R_2$ is trans-alcohol can be prepared according to JO 2004-791-A.

The compounds of formula I wherein Y is —$NR_6$ and $X_1$ is —NCN can also be prepared by heating a thiourea of the formula

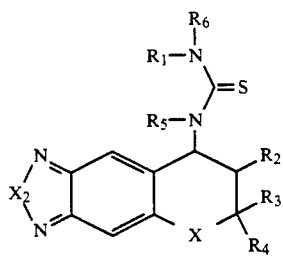
XIV with monosodium cyanamide in the presence of a carbodiimide such as the carbodiimides discussed above, in an organic solvent.

The compounds of formula XVI can be prepared from the amino alcohol of formula III by standard methods (i.e., the Rasmussen and Mozolis references above).

The compounds of formula I wherein Y is $NR_6$ can also be prepared by reacting a compound of the formula

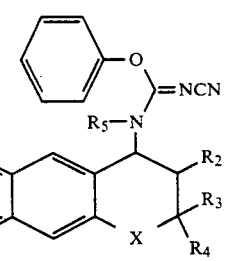
XV with an amine of the formula $R_1R_6NH$   XVI in a polar solvent, such as isopropanol. The compounds of formula XVI are prepared by reacting an amine of formula III with diphenylcyanocarbonimidate.

The compounds of formula I where $X_1$ is —O— and Y is —$NR_6$ can be prepared by treatment of a compound of the formula

XVII with 4-nitrophenylchloroformate to provide an intermediate of the formula

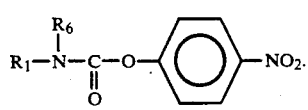
XVIII

Intermediate XVIII can thereafter be reacted with the amine of formula III in an organic solvent, such as dimethylformamide, tetrahydrofuran, acetonitrile or dichloromethane, to provide the corresponding compounds of formula I.

Compounds of formula I wherein $X_1$ and Y are oxygen can be prepared from a compound of formula III by treatment with a chloroformate of the formula

  XIX in an organic solvent and in the presence of an amine catalyst.

Compounds of formula I wherein $X_1$ is oxygen and Y is

, can be prepared by reacting a compound of formula III with an acid of the formula

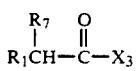  XX (where $X_3$=OH, Cl)
and a carbodiimide or an acyl chloride of formula XX in an organic solvent and a base such as triethylamine and pyridine.

Compounds of formula I wherein X is sulfur can be prepared by treating compounds of formula I wherein $X_1$ is oxygen with Lawesson's reagent or with $P_4S_{10}$ in organic solvents such as tetrahydrofuran and toluene.

If any of the R's in the above reactions contain one or more hydroxy or amino groups, heterocyclo wherein the heterocyclo ring contains an NH such as imidazolyl then the hydroxyl, amino or mercaptan function should be protected during the reaction. Suitable protecting groups include benzyloxycarbonyl, t-butoxycarbonyl, benzyl, benzhydryl, etc. The protecting group is removed by standard means following completion of the reaction.

The compounds of the present invention can have asymmetric centers at carbons 2-4 of benzopyran ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The compounds of the present invention wherein $R_5$ and/or $R_6$ is hydrogen, can exist as a mixture of tautomers represented by the following structures. The tautomeric products are obtained in relative amounts that differ from compound to compound. All forms are included in the scope of formula I.

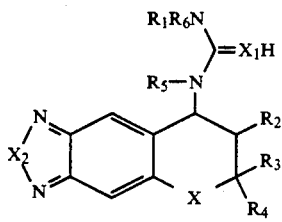  (I')

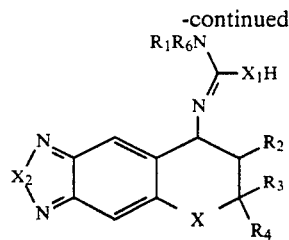  (I")

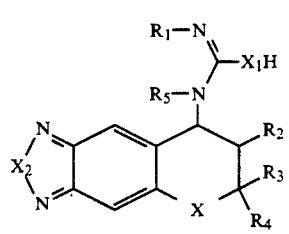  (I''')

Tautomers of formula I similar to I' and I" are also possible wherein Y is O, S and

and are also included in the scope of this invention.

The compounds of formula I and the pharmaceutically acceptable salts act as potassium channel activators. Thus, compounds of the present invention are useful cardiovascular agents, e.g. as anti-arrhythmic agents and antiischemic agents.

As described previously, compounds of formula I are particularly useful as antiischemic agents since they have been found to possess little or no antihypertensive activity. Thus, compounds of formula I are useful for the treatment of ischemic conditions, e.g. myocardial ischemia, cerebral ischemia, lower limb ischemia and the like. The selectivity, i.e., antiischemic activity with little or no antihypertensive activity, means that in the treatment of, for example, ischemic heart, these compounds are less likely to cause coronary steal, profound hypotersion and coronary underperfusion. By little or no vasodilation activity is meant that these compounds have $IC_{50}$ (rat aorta) values greater than that of the potassium channel activator, cromakalim. The "selective" antiischemic agents typically are those having $IC_{50}$ (rat aorta) values >10 times that of cromakalim (i.e., have 1/10 the vasodilatory action) and preferably those having $IC_{50}$ values >50 times that of cromakalim.

Thus, for example, by the administration of a composition containing one (or a combination) of the compounds of this invention, ischemic conditions of a mammalian (e.g., human) host are reduced. A single dose, or preferably two to four divided daily doses, provided on a basis of about 0.001 to 100 mg per kilogram of body weight per day, preferably from about 0.1 to about 25 mg per kilogram per day, is appropriate to reduce ischemic conditions. The substance is preferably administered orally, but parenteral routes, such as the subcutaneous, intramuscular, or intravenous routes or any other convenient delivery system, such as inhalation or intranasal solutions or transdermal patches, can also be employed. The above doses are also suitable for the other cardiovascular and non-cardiovascular uses.

As a result of the potassium channel activating activity of compounds of this invention, these compounds are also useful in the treatment of cardiovascular disorders. For example, compounds of the present invention are useful as therapy for congestive heart failure, as anti-anginal agents, as anti-fibrillatory agents, as thrombolytic agents and in limiting myocardial infarction.

Compounds of the present invention are additionally expected to be useful in the treatment of central nervous system disorders (e.g., Parkinsonism, as anti-tremor agents, epilepsy).

The compounds of this invention can also be formulated in combination with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Preferred compounds are those wherein
X and $X_2$ is O;
$X_1$ is O, NCN;
Y is $NR_6$;
$R_1$ is aryl, arylalkyl;
$R_2$ is H, OH;
$R_3$ and $R_4$ are each alkyl;
$R_5$ is H; and,
$R_6$ is H, alkyl.
Most preferred are those compounds wherein
X is O;
$X_1$ is O;
$X_2$ is O;
Y is NH;
$R_1$ is phenyl, phenylmethyl;
$R_2$ is H, trans-OH;
$R_3$ and $R_4$ are each methyl;
$R_5$ is H; and,
$R_6$ is H.
Specific embodiments of the present invention are described hereinafter in the following examples.

EXAMPLE 1

(trans)-N''-Cyano-N-(7,8-dihydro-7-hydroxy-6,6-dimethyl-6H-[1]benzopyrano[6,7-c][1,2,5]oxadiazol-8-yl-N'-phenylguanidine A. 6-Amino-2,2-dimethyl-2H-1-benzopyran A solution of 6-nitro-2,2-dimethyl-2H-benzopyran (prepared as described in Evans et al., *J. Med. Chem.*) (4.65 g, 22.66 mmoles) and $SnCl_2 \cdot 2H_2O$ (25.57 g, 0.11 mole) in ethanol (46.5 ml) was heated at reflux for 45 minutes. The reaction mixture was poured onto ice/$H_2O$ (180 g), made basic (pH 10–11) with 50% sodium hydroxide solution, and extracted with ethyl acetate. The organic phase was washed with saturated sodium chloride solution, dried over sodium sulfate, and evaporated in vacuo to obtain 3.88 g of the title A compound as a brown oil.

$^1H$ NMR (CDCl$_3$) δ 6.61 (d, J=8.21 Hz, 1H), 6.47 (dd, J=2.35 and 8.21 Hz, 1H), 6.36 (d, J=2.93, 1H), 6.22 (d, J=9.97, 1H), 5.60 (d, J=9.38, 1H), 3.35 (broad s, 2H), 1.39 (s, 6H).

B. 6-Acetylamino-2,2-dimethyl-2H-1-benzopyran

To a solution of the title A compound (3.88 g, 22.14 mmoles) and triethylamine (2.46 g, 24.36 mmoles) in methylene chloride (100 ml) maintained at 0° C. was added acetyl chloride (1.82 g, 23.24 mmoles) over five minutes. The reaction mixture was warmed to room temperature and concentrated under vacuum. The residue was dissolved in ethyl acetate (75 ml), the precipitated amine.HCl was removed by filtration. The filtrate was washed with 5% aqueous hydrochloric acid solution, saturated sodium hydrogen carbonate solution, saturated sodium chloride solution, dried over anhydrous magnesium sulfate, and concentrated in vacuo to obtain 4.85 g of a tan solid. The crude product was recrystallized from hexane/ethyl acetate (3:1) to obtain 3.44 g of the title compound as an off-white solid. The residue recovered from the mother liquor was chromatographed on silica gel eluting with 1:1 ethyl acetate/hexane to afford an additional 0.49 g of the title B product.

$^1H$ NMR (CDCl$_3$) δ 7.52 (broad s, 1H), 7.24 (s, 1H), 7.06 (d, J=8.20 Hz, 1H), 6.69 (d, J=8.21 Hz, 1H), 6.25 (d, J=9.97, 1H), 5.60 (d, J=9.38, 1H), 2.11 (s, 3H), 1.40 (s, 6H).

C.

6-Acetylamino-2,2-dimethyl-7-nitro-2H-1-benzopyran

To a solution of the title B compound (3.93 g, 18.09 mmoles) in glacial acetic acid (17.85 ml) cooled to 8° C. was added 90% fuming nitric acid (1.58 g, 22.6 mmoles, 1.25 eq.). After stirring for 45 minutes at ambient temperature, the reaction appeared approximately 50% complete. The reaction mixture was cooled to 8° C., an additional 1.25 eq. of nitric acid was added. The reaction was stirred for 30 minutes at ambient temperature and poured onto 200 g ice/water. The precipitated orange solid was collected via suction filtration, coevaporated with ethanol, and recrystallized from ethanol to afford 3.43 g of the title C compound as an orange crystalline solid. An additional 0.39 g of product was obtained from the mother liquor by chromatography on silica gel eluting with 3:1 hexane/ethyl acetate.

$^1H$ NMR (CDCl$_3$) δ 10.16 (broad s, 1H), 8.36 (s, 1H), 7.58 (s, 1H), 6.39 (d, J=9.97 Hz, 1H), 5.89 (d, J=9.38 Hz, 1H), 2.25 (s, 3H), 1.45 (s, 6H).

D.
6-Acetylamino-3-bromo-3,4-dihydro-2,2-dimethyl-4-hydroxy-7-nitro-2H-1-benzopyran To a solution of the title C compound (3.41 g, 13.0 mmoles) in dimethyl sulfoxide/water (4:1) maintained at 0° C. was added N-bromosuccinimide (4.16 g, 23.4 mmoles). The reaction was stirred at room temperature for about 4 hours. The reaction mixture was partitioned between ethyl acetate and distilled water. The organic layer was washed with distilled water, saturated sodium hydrogen carbonate solution, saturated sodium chloride solution, dried over anhydrous magnesium sulfate and concentrated in vacuo to obtain 3.88 g of a yellow solid. The crude product was recrystallized from ethanol to afford 2.70 g of the title D compound as a yellow solid. The residue recovered upon evaporation of the mother liquor was chromatographed on silica eluting with 1:1 ethyl acetate/hexane to obtain an additional 0.93 g of product.

E.
6-Amino-3-bromo-3,4-dihydro-2,2-dimethyl-4-hydroxy-7-nitro-2H-1-benzopyran A solution of the title D compound in a mixture of ethanol (35 ml) and 5N hydrochloric acid (35 ml) was heated at reflux for 1.5 hours. The reaction mixture was cooled to room temperature, made basic with 2N sodium hydroxide and extracted with ethyl acetate. The extracts were washed with saturated sodium chloride solution, dried over sodium sulfate and concentrated in vacuo to obtain 3.75 g of red solid. The crude product was recrystallized from ethanol to obtain 2.05 g of the title E compound as a red solid. The residue recovered upon evaporation of the mother liquor was chromatograhed on silica gel eluting with 3:2 hexane/ethyl acetate to afford an additional 0.73 g of product.

F.
6-Amino-3,4-dihydro-2,2-dimethyl-3,4-epoxy-7-nitro-2H-1-benzopyran

To a solution of the title E compound (2.78 g, 8.76 mmoles) in diethyl ether (250 ml) was added powered potassium hydroxide (8.85 g, 0.16 mole). The reaction mixture was stirred at room temperature for 24 hours and partitioned between distilled water and ethyl acetate. The aqueous layer was extracted with ethyl acetate. The combined organics were washed with saturated sodium chloride solution, dried over sodium sulfate and evaporated in vacuo to obtain 1.58 g of the title F compound as a red solid. The product was used in the next step without further purification.

G.
7,8-Dihydro-6,6-dimethyl-7,8-epoxy-6H-pyrano[2,3-f]benzo-2,1,3-oxadiazol-3-oxide To a solution of the title F compound (1.45 g, 6.14 mmoles) in ethanol (130 ml) was added 1N sodium hydroxide solution (10.4 ml) followed by 5.25% sodium oxychloride solution dropwise over 15 minutes. The reaction was stirred at room temperature for 30 minutes, diluted with saturated sodium chloride solution (350 ml) and extracted with ethyl acetate. The combined organics were washed with saturated sodium chloride solution, dried over sodium sulfate, and evaporated in vacuo to obtain 1.42 g of the title G compound as a light brown solid. The product was used in the next step without further purification.

H.
7,8-Dihydro-6,6-dimethyl-7,8-epoxy-6H-pyrano[2,3-f]benzo-2,1,3-oxadiazole To a solution of the title G compound (1.42 g, 6.06 mmoles) in benzene (20 ml) at 60° C. was added triethyl phosphite (1.11 g, 6.67 mmoles, 1.1 eq.) over 15 minutes. The reaction mixture was stirred for three hours at 60° C. The solvent and excess triethyl phosphite were evaporated under high vacuum. The residue was partitioned between 1N sodium hydroxide solution and ethyl acetate. The organic layer was washed with saturated sodium chloride solution, slurried with activated charcoal and filtered through a celite/silica gel pad. The filtrate was dried over sodium sulfate and evaporated in vacuo to obtain 0.99 g of the title H compound as an off-white solid. The reaction product was used in the next step without further purification.

I.
8-Amino-7,8-dihydro-6,6-dimethyl-7-hydroxy-6H-pyrano[2,3-f]benzo-2,1,3-oxadiazole A solution of the title H compound (0.99 g, 4.54 mmoles) in a mixture of ethanol (5 ml), tetrahydrofuran (5 ml) and saturated ammonium hydroxide solution (5 ml) was heated in a thick-walled glass pressure bottle at 60°-65° C. for 42 hours. The volatiles were evaporated in vacuo to obtain 1.02 g of tan solid. The crude material was chromatographed on silica gel eluting with 7.5% methanol in ethyl acetate to obtain 0.69 g of the title I compound as an off-white solid.

$^1$H NMR (DMSO-$d_6$) 6 8.2 (d, J=1.8 Hz, 1H), 7.1 (s, 1H), 5.7 (m, 1H), 3.7 (dd, J=2.3 and 10.0 Hz, 1H), 1.4 (s, 3 H), 1.2 (s, 3 H).

J.
(trans)-N''-Cyano-N-(7,8-dihydro-7-hydroxy-6,6-dimethyl-6H-[1]benzopyrano[6,7-c]-[1,2,5]oxadiazol-8-yl-N'-phenylguanidine A solution of the title I compound (0.43 g, 1.83 mmoles), N-cyano-N-phenylthiourea (0.42 g, 2.38 mmoles, 1.3 eq.) and 1-(3-dimethylaminopropyl)-2-ethylcarbodiimide hydrochloride (0.46 g, 2.38 mmoles, 1.3 eq.) in dimethylformamide (4 ml) was stirred at room temperature for four hours. The reaction mixture was partitioned between 5% aqueous hydrochloric acid solution and chloroform. The aqueous phase was extracted with chloroform. The combined organics were washed with saturated sodium hydrogen carbonate solution, saturated sodium chloride solution, dried over sodium sulfate and evaporated in vacuo to obtain 1.04 g of a tan solid. The crude product was chromatographed on silica eluting with 1:1 ethyl acetate/hexane to obtain 0.32 g of the title compound as an off-white solid (m.p. 219°-220° C.).

$^1$H NMR (DMSO-$d_6$) δ 9.4 (broad s, 1H), 7.9 (broad s, 1H), 7.7 (d, J=7.6 Hz, 1H), 7.4 (m, 4H), 7.2 (m, 2H), 6.1 (broad s, 1H), 5.1 (m, 1H), 3.9 (m, 1H), 1.45 (s, 3H), 1.25 (s, 3H).

Analysis calc'd for $C_{19}H_{18}N_6O_3$. 0.35 $H_2O$: C, 59.33; H, 4.90; N, 21.85; Found: C, 59.70; H, 5.00; N, 21.48.

EXAMPLE 2

(trans)-N-(7,8-Dihydro-7-hydroxy-6,6-dimethyl-6H-[1]benzopyrano[6,7-c][1,2,5]oxadiazol-8-yl)-N'-phenylurea To a solution of 7,8-dihydro-6,6-dimethyl-7-hydroxy-8-amino-6H-pyrano[2,3-f]benzo-2,1,3-oxadiazole (0.25 g, 1.06 mmoles) (prepared as described in part I of Example 1) in ethanol (2.5 ml) at 60° C. was added phenyl isocyanate (0.126 g, 1.06 mmoles). The reaction was heated at reflux for three hours, cooled to room temperature and diluted with isopropyl ether (5 ml). The product slowly crystallized from solution. It was collected via suction filtration and dried under vacuum to obtain 0.18 g of the desired compound as a beige solid. The residue obtained upon evaporation of the mother liquor was chromatographed on silica gel eluting with 1:1 ethyl acetate/hexane to afford an additional 0.16 g of product. The two crops were combined and triturated with isopropyl ether to obtain 0.30 g of the title compound as an off-white solid (m.p. 215°–216° C.).

$^1$H NMR (DMSO-$d_6$) δ 8.80 (s, 1H), 7.87 (s, 1H), 7.47 (d, J=7.62 Hz, 2H), 7.26 (t, J=7.62 Hz, 2H), 7.17 (s, 1H), 6.95 (m, 1H), 6.82 (d, J=7.62 Hz, 1H), 5.85 (d, J=5.87 Hz, 1H), 4.80 (m, 1H), 3.80 (m, 1H), 1.48 (s, 3H), 1.27 (s, 3H).

Analysis calc'd for $C_{18}H_{18}N_4O_4$: C, 61.01; H, 5.12; N, 15.81; Found: C, 60.63; H, 5.18; N, 15.40.

What is claimed is:

1. A compound of the formula

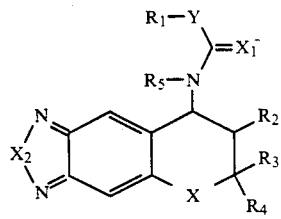

and pharmaceutically acceptable salts thereof,
wherein X is —O—,

or a single bond;
$X_1$ is —O—, —S— or N—C≡N;
$X_2$ is —O— or —NH—;
Y is —NR$_6$, —O—, —S— or

$R_1$ is aryl, arylalkyl, heterocyclo or (heterocyclo)alkyl;
$R_2$ is hydrogen, hydroxy,

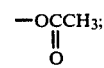

$R_3$, $R_3'$, $R_4$ and $R_4'$ are independently selected from hydrogen, alkyl or arylalkyl, or, $R_3$ and $R_4$ (or $R_3'$ and $R_4'$) taken together with the carbon atom to which they are attached form a 5- to 7-membered ring; with the proviso that if $R_3$ and/or $R_4$ are other than hydrogen, then $R_3'$ and $R_4'$ are each hydrogen;

$R_5$ and $R_6$ are each independently hydrogen, alkyl or arylalkyl; or $R_1$ and $R_5$, or, $R_5$ and $R_6$ or $R_1$ and $R_6$ taken together can form a 5- to 7-membered ring, which may further include an aryl group fused to 2 carbon atoms of such 5- to 7-membered ring; and $R_7$ is hydrogen, hydroxy, alkyl or O-alkyl; wherein the term "alkyl" used in defining various symbols refers to straight or branched chain saturated hydrocarbon radicals having up to eight carbons, the terms "alkoxy" and "alkylthio" refer to said alkyl groups attached to an oxygen or sulfur;

the term "alkenyl" refers to straight or branched chain hydrocarbon radicals having from two to eight carbons and one double bond;

the term "alkynyl" refers to straight or branched chain hydrocarbon radicals having from two to eight carbons and one triple bond;

the term "cycloalkyl" refers to saturated carbocyclic rings of 3 to 7 carbon atoms;

the term "halo" or "halogen" refers to chloro, bromo, iodo and fluoro;

the term "halo substituted alkyl" refers to said alkyl groups in which one or more hydrogens have been replaced by chloro, bromo or fluoro groups;

the term "aryl" refers to phenyl, 1-naphthyl, 2-naphthyl or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, N(R$_9$)CO—R$_9$, N(R$_9$)COCF$_3$, N(R$_9$)CO-amino, N(R$_9$)CO-substituted amino, COR$_9$, COOR$_9$ (wherein R$_9$ is R$_5$, aryl and haloalkyl),

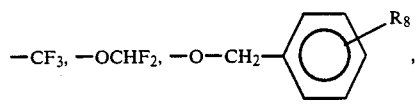

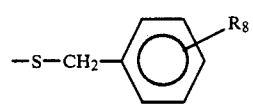

(wherein R$_8$ is hydrogen, alkyl, of 1 to 4 carbons, alkoxy of 1 to 4 carbons, alkylthio of 1 to 4 carbons, halo, hydroxy or CF$_3$), —O—CH$_2$-cycloalkyl, or —S—CH$_2$-cycloalkyl, and di-substituted phenyl, 1-naphthyl, 2-naphthyl wherein said substituents are selected from methyl, methoxy, methylthio, halo, CF$_3$, nitro, amino, and OCHF$_2$;

the term "heterocyclo" refers to fully saturated or unsaturated rings of 5 or 6 atoms containing one or two O and S atoms and/or one to four N atoms provided that the total number of hetero atoms in the ring is 4 or less, wherein the hetero ring is attached by way of an available atom and wherein the term hetero also includes bicyclic rings wherein the five or six membered ring containing O, S and N atoms as defined above is fused to a benzene ring and the bicyclic ring is attached by way of an available carbon atom, which monocyclic and bicyclic rings may be substituted at an available carbon atom with a lower alkyl of 1 to 4 carbons, lower alkylthio of 1 to 4 carbons, lower alkoxy of 1 to 4 carbons, halo, nitro, keto, cyano, hydroxy, amino, —NH-alkyl wherein alkyl is of 1 to 4 carbons, —N(alkyl)$_2$ wherein alkyl is of 1 to 4 carbons, $CF_3$, or $OCHF_2$ or which monocyclic and bicyclic rings may have substituents at two or three available carbons, said substituents selected from methyl, methoxy, methylthio, halo, $CF_3$, nitro, hydroxy, amino and $OCHF_2$; and, the term "substituted amino" refers to a group of the formula —$NZ_1Z_2$ wherein $Z_1$ is hydrogen, alkyl, cycloalkyl, aryl, arylalkyl, cycloalkylalkyl and $Z_2$ is alkyl, cycloalkyl, aryl, arylalkyl, cycloalkylalkyl or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

2. A compound of claim 1 wherein
X and $X_2$ is O;
X is O, NCN;
Y is $NR_6$;
$R_1$ is aryl, arylalkyl;
$R_2$ is H, OH;
$R_3$ and $R_4$ are each alkyl;
$R_5$ is H; and,
$R_6$ is H, alkyl.

3. A compound of claim 1 wherein
X is O;
$X_1$ is O;
$X_2$ is O;
Y is NH;
$R_1$ is phenyl, phenylmethyl;
$R_2$ is H, trans-OH;
$R_3$ and $R_4$ are each methyl;
$R_5$ is H; and,
$R_6$ is H.

4. A compound of claim 1 having the name (trans)-N''-cyano-N-(7,8-dihydro-7-hydroxy-6,6-dimethyl-6H-[1]benzopyrano[6,7-c][1,2,5]oxadiazol-8-yl-N'-phenylguanidine.

5. A compound of claim 1 having the name (trans)-N-(7,8-dihydro-7-hydroxy-6,6-dimethyl-6H-[1]benzopyrano[6,7-c][1,2,5]oxadiazol-8-yl)-N'-phenylurea.

* * * * *